United States Patent [19]

Eftekhar

[11] 4,342,309
[45] Aug. 3, 1982

[54] BOW TYPE TRACTION DEVICE HAVING CORPOREAL INSERTION MEANS

[76] Inventor: Nas S. Eftekhar, 25 Paddock Rd., Hohokus, N.J. 07423

[21] Appl. No.: 223,288

[22] Filed: Jan. 8, 1981

[51] Int. Cl.³ .............................................. A61F 5/04
[52] U.S. Cl. ................................................ 128/84 R
[58] Field of Search ...................... 128/83, 84 R, 84 A, 128/84 B, 84 C, 75, 92 A

[56] References Cited

U.S. PATENT DOCUMENTS 3,088,460 5/1963 Wright ............................... 128/84 R
3,224,440 12/1965 Wright ............................... 128/84 R
3,809,074 5/1974 DeMoude ........................ 128/84 R Primary Examiner—John D. Yasko
Attorney, Agent, or Firm—Sherman & Shalloway

[57] ABSTRACT

A method and apparatus using a bow and pin type traction device in which a pin is passed through the bone in the patient's limb. A bow member is adaptable to drive the pin into the limb as a brace and bit. After the pin is inserted into the limb, the bow member grips the pin on both sides of the limb to apply traction. The dual function of the bow enables the provision of all specialized equipment for installation of the bow and pin in a single unitized packaged kit.

11 Claims, 4 Drawing Figures

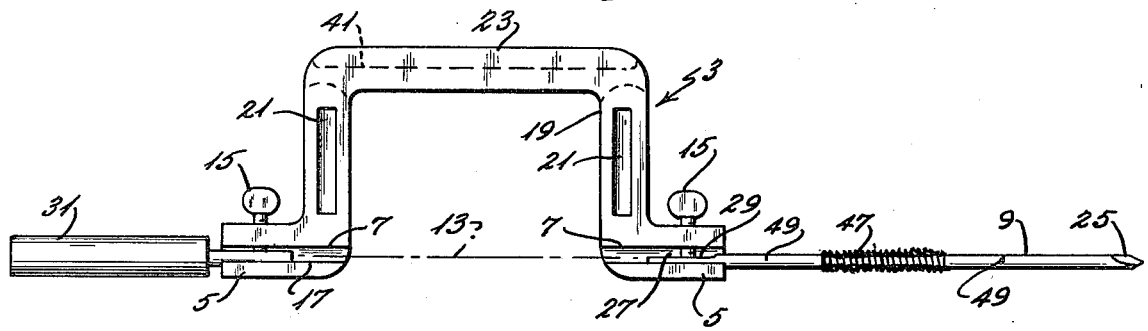
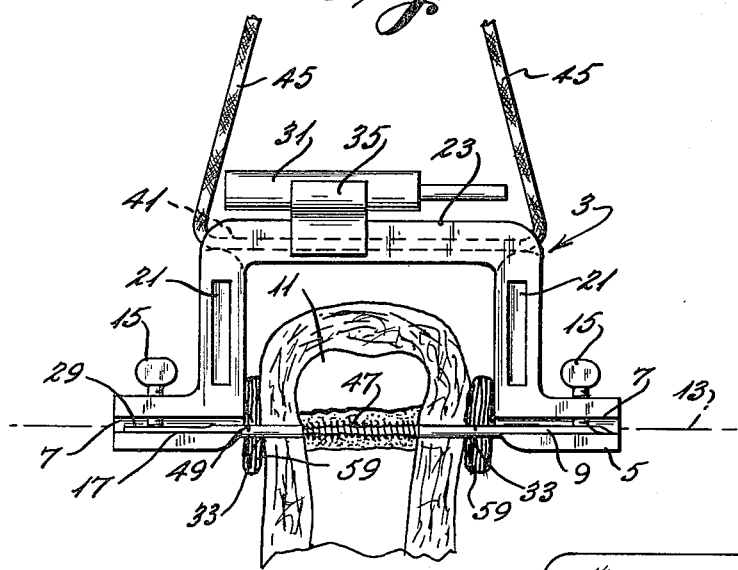
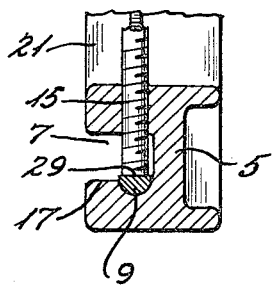
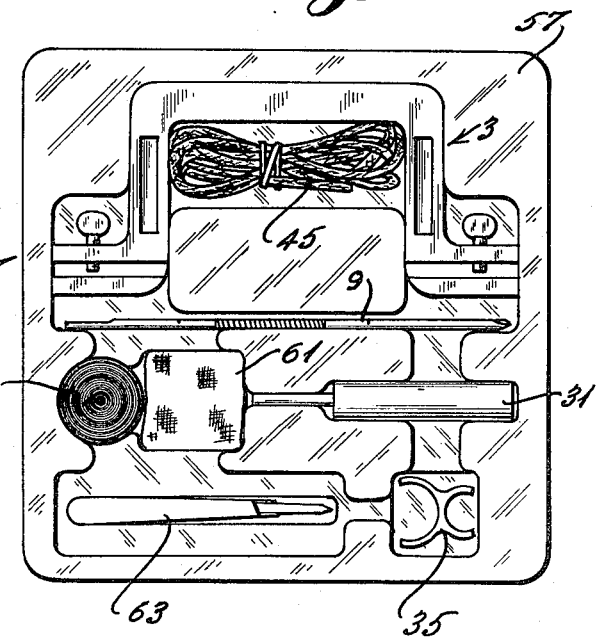

BOW TYPE TRACTION DEVICE HAVING CORPOREAL INSERTION MEANS

BACKGROUND OF THE INVENTION

1. Field of the Invention

This invention is directed to the application of tractive force to the skeletal frame of the patient.

Tractive force is applied in various manners. Often, externally applied skin traction may be used to maintain the desired skeletal tractive force for the necessary amount of time. While this technique causes a minimum of discomfort and minimizes risks of infection, the amount of force applied by this method, particularly over any considerable time period, is limited.

In some instances, tractive force may be applied by applying leverage with an undamaged extremity member, particularly when the undamaged extremity member is located further from the torso than the damaged member and the undamaged extremity may comfortably be held at a more or less fixed angle such as 90°.

In other cases, particularly in cases of compound fractures, it may be necessary to surgically expose bone tissue and directly apply a splint to the damaged bone. By bridging the fracture with the splint, the bone segments are maintained at the desired separation distance from one another. While this procedure may be necessary in some instances, there are other instances where bone healing would likely take place without the application of such a splint if tractive force could be applied to the bone.

In cases where traction is to be directly applied to the skeletal structure but it is not otherwise necessary to directly apply a splint to the damaged bone, a technique using a pin and bow has been used. The pin is inserted into the patient's extremity so as to pass through a portion of the bone to which tractive force is to be applied. The pin is inserted so that both ends extend beyond the skin of the patient and these ends are gripped by a bow member. The bow member, in turn, has a cord attached thereto and tractive force is applied by the cord, usually by passing the cord through a pulley and suspending an appropriate amount of weight at the opposite end of the cord which hangs down from the pulley. The pin and bow technique permits the application of traction directly to a patient's bone while minimizing the amount of surgical procedure required for the application of such traction. In many cases, this technique also simplifies the application of traction over externally applied traction techniques in that the patient is given more flexibility within his confined situation.

The nature of bone fractures are such that there are many cases in which traction is advantageously applied in a medical emergency operating room, or even in a remote location such as an ambulance. In such situations, it is desirable that the amount of preparation required for surgery be minimized. This preparation not only includes the appropriate sterilization of the items, but also the collection of all of the equipment needed for this type of surgery. It is desirable that all of the equipment needed for the surgical procedure be readily available in a unitary package, not only because of the time factors involved in the emergency situation, but also because a set of equipment requiring a minimum of storage space can be more readily stored for rapid access to the equipment, particularly in locations where space is limited.

The use of the pin requires that some means be provided for the insertion of the pin in the body. This is normally accomplished by a drill such as a brace and bit. Usually the pin is formed with appropriate cuts or grooves so as to facilitate boring into the patient's body and particularly into the patient's bone. The pin is therefore functional as the bit in the brace and bit. The brace and bit has the advantage that rotational movement of the bit is relatively slow, thereby reducing necrosis of the tissue surrounding the puncture site.

DESCRIPTION OF THE PRIOR ART

As noted above, various techniques have been used to apply traction to the human body, including the bow and pin technique. The bow element of the prior art devices is usually a wishbone-shaped device which is attached to the pin after the pin has been inserted into the bone. Attachment means are provided on the bow which permit the bow to be secured to the pin so as to prevent lateral movement of the bow on the pin. These devices had the primary disadvantage that they did not provide a means for forcing the entry of the pin into the patient's limb and therefore required the use of a separate drilling device such as a drilling brace. For this reason, the bow type traction devices of the prior art were more difficult to store in such a way as to be immediately accessible in an emergency situation. This was because, in addition to the traction device, it was necessary to store or collect the drill brace.

SUMMARY OF THE INVENTION

Accordingly, it is an object of this invention to provide a convenient means for applying traction using a pin in which the inconvenience of storing and retrieving specialized equipment is reduced.

It is a further object of the present invention to provide a means for applying traction to the human body through a pin which is inserted through a patient's bone tissue and in which tractive force is applied to the pin from each end of the pin by means of a bow member which is, in turn, connected to a cord, pulley and weight, in which the provision of other specialized equipment is not required.

It is a further object of this invention to provide a bow member for a bow and pin assembly, which bow can be used as a driving member to drive the pin into the patient's body.

It is a further object of this invention to provide a method for applying traction to a patient using a bow and pin, in which the bow is first used with the pin in a brace and bit mode for inserting the pin into the patient's limb and in which the bow is then reconnected to the pin so that the ends of the bow grip the ends of the pin as the ends of the pin extend beyond the patient's limb so that the bow can then be used to apply traction to the pin.

It is still a further object of this invention to provide a method for removing the pin of a bow and pin combination from a patient's limb, in which the bow can be arranged with the pin so as to form a brace and bit for the purpose of removing the pin.

These and other objects are met by this invention, in which a means is provided for applying traction to the human body through a pin which is inserted through a patient's bone tissue and in which tractive force is applied to the pin from each end of the pin by means of a bow member which is, in turn, connected to a cord, pulley and weight, in which the provision of other specialized equipment is not required.

In further aspect of this invention, a bow member is provided for an assembly using a bow and pin, in which the bow can be used as a driving member to drive the pin into the patient's body.

In another aspect of this invention, a traction device having pin and bow members is provided in which the bow member has an insertion means in each end portion thereof and a securing means to secure the pin to the end portions, and in which the pin can be arranged with the bow member so as to form a brace and bit.

In another aspect of this invention a bow and brace assembly is improved by having the bow adaptable to cooperate with the pin to form a brace and bit. A bow is adaptable so that the bow and pin may be used as a brace and bit so that the bow and pin may be provided in a package which may include all of the items necessary for an emergency medical facility to install the bow and pin on the patient's limb.

In a further aspect of this invention such a bow and pin combination further includes a handle extension for the end of the bow to facilitate the use of the bow and pin in a brace and bit mode.

In another aspect of this invention a method is provided for applying traction to a patient using a bow and pin, in which the bow is first used with the pin in a brace and bit mode for inserting the pin into the patient's limb and in which the bow is then reconnected to the pin so that the ends of the bow grip the ends of the pin as the ends of the pin extend beyond the patient's limb so that the bow can then be used to apply traction to the pin. This invention further provides a means wherein when it is desired to remove the pin of a bow and pin combination from a patient's limb, the bow can be arranged with the pin so as to form a brace and bit for the purpose of removing the pin.

BRIEF DESCRIPTION OF THE DRAWINGS

FIG. 1 shows the assembly according to the present invention arranged in a brace and bit mode.

FIG. 2 shows the apparatus according to the present invention arranged in its tractive force applying mode.

FIG. 3 shows the various components used in the application of the bow and pin procedure according to the invention arranged in a kit.

FIG. 4 is an end view of the apparatus taken along section A—A of FIG. 1.

DETAILED DESCRIPTION OF THE PREFERRED EMBODIMENT

Referring to FIGS. 1-4, the bow and pin assembly according to the invention utilizes a rigid bow 3 having two end portions 5, each end portion having an insertion channel 7 therein. As can be seen, particularly in FIG. 2, a pin 9 is received in the insertion channel 7, thereby permitting the bow to grip, by means of the pin, a patient's bone tissue 11.

The bow is preferably made of plastic and the pin is made of a biologically compatable metal alloy such as surgical stainless steel. As can be seen in FIGS. 1, 2 and 4, the insertion channels 7 are aligned along a bow axis 13. When the pin 9 is placed in one of the insertion channels 7, the axis 13 coincides with the center axis of the pin 9. As shown in FIG. 1, a pair of securing means, shown as thumb screws 15, are operable to secure an item, such as the pin 9, which is inserted into the insertion channel. Each insertion channel 7 is provided with a raised lip 17 which, in the views of FIGS. 1 and 2, partially obscures the pin 9. The raised lip 17 functions to prevent lateral movement of an item such as pin 9 which is inserted into the insertion channel 7. Extending between the end portions 5 of the bow 3 is a center portion 19. The center portion 19 consists of a pair of legs 21 and a grip 23. Each leg 21 extends from an end portion 5 to the grip 23 in a direction perpendicular from the axis 13. The legs 21 are made equal in length so that the grip 23 is positioned away from the axis 13 and parallel thereto.

The pin 9 is provided with a distal end 25 and a driven end 27. The distal end 25 is preferably a cutting tip and the driven end 27 preferably has at least one flattened side 29 thereon.

Referring to FIG. 1, if the pin 9 is inserted into the insertion channel 7 of the bow 3 at the driven end 27 so that the distal end 25 extends away from the bow 3, the bow 3 and pin 9 are placed in a brace and bit mode and function as a conventional brace and bit drill. A handle 31 is provided so that the insertion channel 7 located in that end portion 5 which is not holding the pin 9 may receive the handle 31. The handle provides an extension and gripping portion for that end 5 which is not holding the pin 9. Potentially, the handle 31 could be included integrally with the bow 3 and therefore would not have to be detachably inserted into the insertion channel 7. However the detachable feature of the handle 31 eliminates what would otherwise be an unnecessary protrusion extending from the assembly and which could be inconvenient when the assembly is attached to the patient.

When it is desired to insert the pin 9 into the patient, incisions are made at the intended points of intersection 33 of the patient's skin and the pin 9. The intersection is chosen so that the pin will avoid any synovial lining, and so that the pin will pass through a large amount of compact bone. The driven end of the pin 9 is inserted into one portion 5 and is secured by the thumb screws 15 so as to place the pin 9 and bow 3 in a brace and bit mode. The handle 31 is secured to the opposite end portion 5. The assembly is then drilled into the patient's limb until the pin 9 extends approximately equidistantly on each side of the patient's bone tissue 11. The thumb screw 15 holding the pin 9 and the thumb screw 15 holding the handle 31 are then loosened and the bow 3 is ready for insertion over the pin 9 in order to place the apparatus in a traction mode.

Referring to FIG. 2, the bow 3 is placed over the pin 9 so that the pin 9 is received by both insertion channels 7. The diameter of the insertion channels 7 is large enough so that the pin 9 can be passed over the raised lips 17 so as to laterally move into the insertion channels 7. With the pin 9 in the insertion channels 7, the bow 3 is positioned about the axis 13 so that the grip 23 is located, with respect to the axis 13, in the intended direction of tractive force. The thumb screws 15 are then tightened so as to prevent lengthwise movement of the pin 9 with respect to the bow 3. The handle 31 is secured to the grip 23 by means of a handle clip 35. The handle clip 35 is merely a resiliently flexible clip member which readily attaches itself simultaneously to both the grip 23 and the handle 31.

The bow 3 is provided with a cord receiving bore 41 which passes through the bow 3 at the grip 23 and is parallel to the axis 13 of the end portions 5. The cord receiving bore 41 is preferably aligned with the grip 23 in such a way that the bore 41 is partially opened along the portion of its length which extends between the legs 21. This permits the cord material to be threaded through the bore 41 more easily. A traction cord 45 is threaded through the cord receiving bore 41 and the traction cord 45 may then be tied and passed over a pulley (not shown) to be connected to a weight (not shown) in a conventional manner.

The pin 9 is preferably provided with a threaded mid-portion 47 and location markings 49. The threaded portion 47 is intended to engage the patient's bone 11. In order to aid the surgeon in the proper positioning of the pin 9 so that the threaded mid-portion 47 is so located, the location markings 49 are equidistantly located from the threaded mid-portion 47. The surgeon merely sights the locations markings 49 in order to judge the proper degree of insertion.

It is to be understood that a wide variety of bone pins could be used in this procedure. Any bone pin suitable for traction could be used provided that it includes at least one means at the driven end 27 to cooperate with the securing means 15 in preventing axial rotation of the pin 9 with respect to the bow 3, at least in the brace and bit mode of operation.

When it is desired that the pin 9 be removed, the traction cord 45 is disconnected from the bow 3 and the thumb screws 15 are loosened. The bow 3 is then removed from the pin 9. The handle 31 is secured to one end portion 5 of the bow 3 and the other end portion 5 is secured to the driven end 27 of the pin 9. The bow 3 and pin 9 are then in the brace and bit mode of operation. Prior to removal of the pin 9 from the patient, the distal end 25 of the pin 9 must be thoroughly cleaned and sterilized. The surgeon then effects counterclockwise rotation of the bow 3 along the axis 13, as viewed from the handle 31, thereby permitting the surgeon to quickly remove the pin 9 from the patient.

In order to facilitate handling and storage of the traction apparatus, the apparatus is packaged in a kit 55, as shown in FIG. 3. The kit includes a plastic tray 57 into which are separately located the bow 3, the pin 9, the handle 31, the handle clip 35 and the traction cord 45. Additionally, rolled gauze 59, flat gauze 61 and a scapel 63 are included in the kit 55. While it is possible to include a container of sterilizing solution in the kit, it is not considered necessary because this type of solution would normally be readily available at the location of surgery. While the scapel 63 and gauze 59, 61 are probably also readily available, these items are disposable and therefore are included in the kit 55. The kit 55 is provided with a cover (not shown) which is hermatically sealed to the tray 55. The kit 55 is exposed to a minimum of 2.5 M rad of gamma radiation in order to sterilize the entire kit. If accidental contamination of the bow 3 takes place, it is of no consequence as long as the pin 9 itself remains sterile.

EXAMPLE

In a typical embodiment, the bow 3 extends 25 cm. along the axis 13, the bow 3 extends 12 cm. as measured perpendicular to the axis 13 and the distance along the axis between the two end portions 5 is 12.5 cm., as is the distance between the two legs 21 or the free length of the grip 23. The distance between the axis 13 and that side of the grip 23 nearest to the axis 13 is 8 cm. Taking into account the thickness of the grip 23 as 2 cm., the bow 3 would therefore have a crank radius extending from the axis 13 to the center of the grip which is 9 cm.

The pin 9 is preferably 22.9 cm. long, and is available in several diameters, ranging from 2 mm. to 4.8 mm. The preferred diameter is 3.96 mm. The preferred pin, as previously stated, has a threaded mid-portion 47. The preferred length of the threaded mid-portion 47 is 6.0 cm., including a self-tapping tapered part, with the remaining part of the threaded mid-portion being 4.7 cm. long. The preferred diameter of the threaded portion in a 4 mm. pin is 4.08 mm.

These dimensions allow the kit 55 enclosed in the tray 57 to be 27 cm. × 27 cm. having a thickness of approximately 3.5 cm. It can be readily seen that the kit 55 is compact and can be made readily stackable.

It can readily be seen that various modifications of the disclosed apparatus can be made, while still retaining the inventive concepts expressed herein. For example, if the handle 31 is made non-removable from the bow 3, it is possible to provide a securing means 15 only at the end portion 5 which is furthest from the handle. Therefore, the invention should be considered limited only by the claims, and not to the specific preferred embodiment herein described.

What is claimed is:

1. A traction device for providing skeletal traction application to a limb of a patient, comprising:
   (a) an elongate traction pin, comprising a driven end and a distal end;
   (b) a bow member comprising first and second end portions connected by a center portion, the end portions being aligned along a bow axis and the center portion extending between the two ends and away from the bow axis;
   (c) an insertion channel in each of the end portions of the bow member, the insertion channels being adapted to receive the pin so that the center axis of the pin generally coincides with the bow axis; and
   (d) a securing means associated with at least one of the end portions of the bow, the securing means being operable to prevent the pin from moving relative to the bow member when an end of the pin is in the end of the bow member having said securing means;
   (e) a handle, the handle being fitted to one end of the bow at least when the other end of the bow is holding the driven end of the pin, wherein the bow may receive the driven end of the pin in one of the bow end portions and cooperate with with the pin and the handle to function as a bit and brace to insert the pin through the patient's limb with each end portion of the pin extending outside the patient's limb, and the bow may receive an end portion of the pin in each of the end portions of the bow to cooperate with the pin to effect traction on the limb by means of a conventional system of a cord, weight and pulley.

2. The device of claim 1 wherein the pin is provided with a threaded portion, the threaded portion being located between the two end portions, and the threaded portion facilitating the penetration of the pin into patient's limb, the threaded portion further acting to retard the pin from laterally moving along the center axis when tractive force is being applied, and the threaded portion further functioning to facilitate the removal of the pin when desired, the removal being effected by arranging the bow and pin in the brace and bit configuration.

3. The device of claims 1 or 2 wherein the handle is detachable from the bow, and a clip means is provided, the clip means being adapted to retain the handle on the center portion of the bow so as to store the handle on the bow during the time that the traction is being applied to the patient.

4. The device of claim 1 wherein the bow, the handle and the pin are provided in a sterile kit, the kit further comprising a scapel and a traction cord, and wherein the ability of the bow and pin to function in the brace and bit mode enables the kit to supply all of the provisions necessary for an emergency medical facility to apply limb traction, without the requirement that any further specialized equipment be stored and without the requirement of a large amount of storage space.

5. In a bow type skeletal traction device for providing skeletal traction application by means of an assembly using a cord through which tractive force is applied by means of pulleys and weights, in which the assembly comprises a pin which is inserted through a patient's bone, and a bow member which connects the pin to the cord, the improvement comprising:
   (a) the pin having distal and driven end portions;
   (b) the pin having insertion facilitating means thereon, the insertion facilitating means exerting a force urging the pin through the patient's body tissues when the pin is rotated about a center axis along its length;
   (c) the bow comprising a generally U-shaped center portion with first and second end portions extending outwardly from the legs of the U-shaped center portion;
   (d) a handle; and
   (e) an insertion channel in the first end portion, and an insertion channel in the second end portion, each insertion channel being adapted to releasably grip the pin, the insertion channels being further adapted so that,
   when only the driven end of the pin is gripped by one of the insertion channels and the pin is positioned so that the distal end projects from the driven end in a direction opposite the other insertion channel and the handle is fitted into the other insertion channel, the bow cooperates with the handle and the pin to function as a brace and bit, thereby facilitating the penetration of the pin into the patient's body, and
   when the pin has been penetrated into the patient's body so that both the distal and driven ends of the pin protrude from the patient's body, the pin may be gripped by both insertion channels so that the bow cooperates with the pin to permit tractive force to be exerted on the patient in a conventional manner by the cord, the pulleys and the weights.

6. The improved device of claim 5 wherein the pin is provided with a threaded portion, the threaded portion being located between the two end portions and the threaded portion facilitating the penetration of the pin into patient's limb, the threaded portion further acting to retard the pin from laterally moving along the center axis when tractive force is being applied, and the threaded portion further functioning to facilitate the removal of the pin when desired, the removal being effected by arranging the bow and pin in the brace and bit configuration.

7. The improved device of claim 5 wherein the bow, the handle and the pin are provided in a sterile kit, the kit further comprising a scapel and a traction cord, and wherein the ability of the bow and pin to function in the brace and bit mode enables the kit to supply all of the provisions necessary for an emergency medical facility to apply limb traction, without the requirement that any further specialized equipment be stored and without the requirement of a large amount of storage space.

8. A bow member adapted for use in a traction device, the bow being adapted to receive at two end portions thereof a bone pin suitable for traction and the bow being adapted to receive at a center portion thereof a traction cord to which tractive force is applied, wherein the bow is further provided with a center section extending between the two end portions, the center section comprising a pair of legs and a grip, each leg extending between one of the end portions and the grip in such a manner as to locate the grip separate from and parallel to an axis running through the end portions, the bow further comprising a pin-receiving channel in each end portion, the pin-receiving channel being along said axis and having at least one securing means for releasably securing the pin to the bow, and the bow being adapted to retain the pin at one of the two end portions and a handle at least temporarily attached to the other end portion so that the bow may be operated as a manually turned drill brace in order to insert the pin into a patient's limb.

9. A method for applying traction to a patient's limb, the method comprising securing a pin to a U-shaped bow member having two ends, the pin being secured to one of the ends so as to extend away from the other end and so that a center axis of the pin passes through both ends; rotating the bow about the center axis with the pin directed against the patient's limb, thereby causing the pin to penetrate the patient's limb until the pin extends from both sides of the limb; releasing the bow from the pin; securing the bow to both ends of the pin with the bow partially encircling the limb; attaching a cord to the bow and applying tractive force to the cord.

10. A bone traction kit for applying traction to a patient in need thereof, the kit comprising a bow, a pin and a handle to enable the bow and pin to be used as a brace and bit, wherein the bow and pin cooperate in an insertion mode to insert the pin into the patient's limb; and in a traction mode the bow grips the pin so as to enable force applied to the bow to be transmitted to the pin, enabling the pin to apply the force directly to the patient's bone tissue as tractive force.

11. The kit of claim 10, further comprising a scapel and a traction cord, wherein the bow, the pin, the scapel and the traction cord are enclosed in a single package and contents of the package are provided in a sterilized form.

* * * * *